United States Patent

Wheatley et al.

[11] Patent Number: 5,206,030
[45] Date of Patent: Apr. 27, 1993

[54] FILM-FORMING COMPOSITION AND USE FOR COATING PHARMACEUTICALS, FOODS AND THE LIKE

[75] Inventors: Thomas A. Wheatley, Richboro, Pa.; Clayton I. Bridges, Jr., Somerset; Carl R. Steuernagel, Medford, both of N.J.

[73] Assignee: FMC Corporation, Philadelphia, Pa.

[21] Appl. No.: 484,309

[22] Filed: Feb. 26, 1990

[51] Int. Cl.$^5$ .................................................. A61K 9/16
[52] U.S. Cl. ..................................... 424/490; 424/439; 424/474
[58] Field of Search ........................ 424/490, 439, 474; 106/181, 196

[56] References Cited

U.S. PATENT DOCUMENTS

| | | | |
|---|---|---|---|
| 3,482,011 | 12/1969 | Bohrer | 264/207 |
| 4,543,370 | 9/1985 | Porter | 523/100 |
| 4,683,256 | 7/1987 | Porter et al. | 524/285 |
| 4,720,378 | 1/1988 | Forse | 424/6 |
| 4,888,420 | 12/1989 | Steiner | 536/64 |
| 4,983,730 | 1/1991 | Domeshek | 106/196 |

OTHER PUBLICATIONS

The Science of Surface Coatings; H. W. Chatfield, Ed. 1962, pp. 453–454.

*Primary Examiner*—Thurman K. Page
*Assistant Examiner*—D. Gabrielle Phelan
*Attorney, Agent, or Firm*—Robert D. Jackson; Patrick C. Baker

[57] ABSTRACT

A water-dispersible, particulate film-forming composition is produced by blending a mixture of particles of water-soluble cellulose acetate; pigment particles, a plasticizer for the water-soluble cellulose acetate, and a surfactant. The composition is useful as a film-forming material for coating solid pharmaceutical forms.

15 Claims, No Drawings

FILM-FORMING COMPOSITION AND USE FOR COATING PHARMACEUTICALS, FOODS AND THE LIKE

FIELD OF THE INVENTION

This invention relates to water-dispersible solid film-forming compositions for use in coating foods and pharmaceuticals and the like. More particularly, the invention is concerned with such film-forming compositions in which the film-forming component is a water-soluble cellulose having improved coating properties.

BACKGROUND OF THE INVENTION

It is well known in the art to envelop solid pharmaceutical materials, tablets, granules and seeds, for example, in a film covering as protection against oxidation, moisture, light, abrasion, rough handling, etc. A pigment is usually present as added protection against light and as a color aid for product identification. The film should be free of roughness, irregularities, cracks or mottled colorations. Film smoothness is important as an aid in swallowing. A hard, shiny surface is desirable for an attractive appearance. Of course, films and coating compositions for ingestion must be edible or physiologically compatible.

Film-forming compositions for coating pharmaceutical tablets preferably contain as the film-forming element, a film-forming resinous material, either naturally occurring or synthetic. Normally, film-forming compositions are applied as a liquid coating formulation comprising a liquid carrier medium having dispersed or dissolved therein the film-forming components. The liquid medium can be an organic solvent or water or a combination of both. Water is preferred owing to the risk of fire and toxicity from organic solvents. Also having to comply with governmental safety standards pertaining to the transportation and handling of industrial chemicals is another minus factor against solvent use.

Generally speaking, application of the liquid coating formulation is effected by spraying dry pharmaceutical forms in rotation in a coating pan or in a fluidized air bed. After evaporation of the liquid medium, the film coated pharmaceuticals are recovered.

As a commercial product, liquid coating compositions are unsatisfactory because of the high transportation costs due to the weight of the liquid carrier. Clearly, it is more practical and economical to ship coating compositions in dry form which can be reconstituted with the appropriate solvent or liquid by the pharmaceutical customer.

An example of a dry film-forming pharmaceutical coating composition and one which is made commercially is described in U.S. Pat. Nos. 4,543,370 and 4,683,256 to Porter et al. and assigned to Colorcon, Inc. In preparing such coating composition, the initial step consists in the high intensity blending of polymer and pigment particles in the presence of a plasticizer and optionally a surfactant. The resulting powder is then fine ground, after which it can be mixed with a solvent or water to provide a coating dispersion for application to tablets or other pharmaceutical forms. On drying, a uniform film is said to be produced on the coated substrate.

Film-forming polymers used in formulating the coating compositions of the patents include both water-soluble and water-insoluble types. Coating dispersions produced from the water-soluble polymers comprise an aqueous solution of the polymer in which are suspended the pigment particles. Water-soluble, film-forming polymers are advantageous in that coating dispersions can be prepared therefrom without the need for organic solvents and their attendant hazards.

The list of water-soluble, film-forming polymers enumerated in the cited patents are: hydroxypropylmethylcellulose, hydroxypropylcellulose, polyvinylpyrrolidone, methylcellulose and sodium ethylcellulose sulfate.

Although an advance in the art, the pharmaceutical coating system of the Colorcon patents is not entirely satisfactory for providing film coatings from solvent free aqueous dispersions owing to certain deleterious characteristics of the water-soluble polymers. For instance, hydroxypropyl-cellulose and polyvinylpyrrolidone produce sticky or tacky films on tablets when coated with aqueous dispersions of these polymers. Methocel is sometimes used but the film coatings tend to be dull and opaque. As far as sodium ethylcellulose sulfate is concerned, it is not normally used as a coating material.

Hydroxypropylmethylcellulose (HPMC), on the other hand, does give smooth transparent tack-free films from aqueous coating dispersion. It is the preferred polymer for coating pharmaceutical forms with the water-dispersible powders of the Colorcon patents. In fact, Colorcon manufactures and sells such dry HPMC film coating compositions under the trademark Opadry. However, coatings produced from HPMC-based Opadry powders are not as stable to moisture and temperature as might be desired. As a consequence, Opadry coated pharmaceuticals tend to deteriorate if exposed much above ambient humidity and temperature.

SUMMARY OF THE INVENTION

It has now been discovered that pharmaceutical films having unexpectedly high stability to moisture and temperature can be realized by using water-soluble cellulose acetate (WSCA) as the film-forming polymer in the above described coating system of the Colorcon patents.

DETAILED DESCRIPTION

Generally speaking, the present invention is carried out using the formulation technique of the Colorcon patents except that the film-forming polymers therein is replaced with WSCA. Typically, the procedure consists in mixing the WSCA and powdered pigment such as titanium dioxide in a V blender, a P-K blender with an intensifier bar or other comparable mixing device. An intimate mixture of a plasticizer and a surfactant is then added to the blender while maintaining agitation to form a coating composition. The resulting mixture is then passed through a grinder whereby there is produced a fine powder. This product is suitable for shipping in dry form for dispersion in water by the pharmaceutical manufacturer at the point of destination. The dispersion can then be applied to tablets and dried to provide a uniform and durable film envelope on the tablets.

WSCA is a known material which is produced by the sulfuric acid catalyzed hydrolysis of secondary cellulose acetate at slightly elevated temperatures; see U.S. Pat. No. 3,482,011. It can be obtained in various viscosity grades from the Hoechst-Celanese Corporation, Charlotte, N.C.

Any of the pigments heretofore used in making coating dispersions for coating tablets and the like may be used in the dry coating mixture of this invention. Examples are FD&C and D&C lakes, titanium dioxide, magnesium carbonate, talc, pyrogenic silica, iron oxides, channel black, and insoluble dyes. Also suitable are natural pigments such as riboflavin, carmine 40, curcumin, and annatto. Other examples are listed in Jeffries U.S. Pat. No. 3,149,040 and Butler et al. U.S. Pat. No. 3,297,535, as well as in Colorcon U.S. Pat. No. 3,981,984. All these patents are incorporated herein by reference.

Exemplary of the polymer plasticizer for use in the dry coating mixture of the invention are polyethylene glycol, for example, polyethylene glycol having a molecular weight of 200 to 8000 (Carbowax ® by Union Carbide Corporation), glycerin, propylene glycol, Triacetin (glyceryl triacetate), acetylated monoglyceride, and triethylcitrate, tributylcitrate and acetyltriethylcitrate.

The polymer plasticizer, to soften the polymer and make it less brittle, may be a liquid or a solid plasticizer, and preferred plasticizers are liquid such as polyethylene glycol 400 and glycerin.

The surfactant may be, for example, a solid powder surfactant such as Aerosol OT (dioctyl sodium sulfosuccinate by American Cyanamid Company) which is preferably used with the liquid polyethylene glycol, 400, or Tween 80 (polysorbate 80 by ICI America, Wilmington, Del.) which is a liquid and is preferably used with a solid plasticizer such as the polyethylene glycol 3350 and 8000.

Blending and processing of the ingredients is generally facilitated where either the plasticizer or surfactant or both is a liquid under mixing conditions. In some instances, the surfactant, as separate component, may be dispensed with since the plasticizer is a liquid and may exhibit surfactant properties. Aqueous dispersal of the dry composition is effected more readily in the presence of a surfactant compound.

In the dry coating composition, about 50% to about 90%, preferably about 80% to about 90% is polymer; about 2% to about 40%, preferably about 5% to about 10% is plasticizer; about 0% to about 20%, preferably about 5% to about 7.5% is pigment and when present separately about 0.2% to about 2.0% surfactant. The components in the dry blend are on a 100% by weight basis.

The film-forming composition can be used to coat pharmaceuticals such as tablets, seeds, granules, pellets, soft and hard gelatin capsules and the like.

The aforementioned pharmaceutical dosage forms comprise drug classes such as multivitamins, multivitamins with minerals, prenatal vitamins, vitamins A and D, $B_1$, $B_2$, $B_6$, $B_{12}$ and vitamin B complex with vitamin C. Additional drug classes include:

Analgesics—acetaminophen, aspirin, ibuprofen, ketoprofen and the like, indomethacin, naproxen, acetaminophen with codeine and acetaminophen with propoxyphene napsylate.

Antibiotics—erythromycin, cephalosporins, etc.

Antiepileptics—phensuximide, phenytoin sodium and valproate sodium.

Antihistamines—chlorpheniramine maleate, diphenhydramine hydrochloride, triprolidine hydrochloride, etc.

Cough and Cold Drugs—dextromethorphan hydrobromide, ephedrine sulfate, guaifenesin, phenylpropanolamine hydrochloride, promethazine hydrochloride, and pseudoephedrine hydrochloride.

Cardiovascular Drugs—captopril, chlorthiazide and hydrochlorthiazide, diltiazem, nadolol, papaverine hydrochloride, procainamide hydrochloride, propranolol hydrochloride, quinidine gluconate, quinidine sulfate, etc.

Electrolytes—potassium chloride.

Gastrointestinal Drugs—cimetidine, loperamide hydrochloride and ranitidine.

Respiratory Drugs—albuterol sulfate, aminophylline, theophylline, etc.

Reference is now made to the following nonlimiting examples.

EXAMPLE 1

Dry Film-Forming, Water-Dispersible Powder

Following the procedure given for Example 1 of U.S. Pat. Nos. 4,543,370 and 4,683,256, a blend of 700 g of low viscosity (LV) WSCA and 350 g of medium viscosity (MV) WSCA for a total WSCA of 1050 g was combined with 525.0 g of titanium dioxide in a 16 quart P-K "V" blender with intensifier bar. The ingredients were blended without the "I" bar for 15-½ minutes. With the "I" bar on, there was added a solution of 3.5 g of dioctyl sodium sulfosuccinate (surfactant) and 105.0 g of polyethylene glycol 400 (plasticizer) prepared by mixing the components at low heat until a clear solution was obtained. Blending was continued for one minute after addition of the surfactant/plasticizer solution. The resulting mixture was then ground to a fine powder by passing it through a Fitz mill with 1526-0014 screen and hammers.

A coating dispersion containing 15% solids by weight was prepared by stirring the fine powder in water and the dispersion applied to aspirin tablet (ASA) cores. After drying, a highly uniform film envelope was formed on the tablets. The dispersion was applied to the ASA cores in a 24" Accela-cota Perforated Pan. Coating conditions are given below

| Spray Coating Equipment | |
| --- | --- |
| Pan | 24" Accela-Cota |
| Baffles | 4 straight & 4 mixing |
| Pump | Masterflex 7562-10 |
| Pump heads | Two 7015 |
| Spray guns | Two SS 7310-1/4 JAU |
| Fluid caps | 1.0 mm |
| Air caps | 134255-45° SS |
| Spray Coating Conditions | Range |
| Batch size (kg) | 10 |
| Spray rate (ml/min/gun) | 15–16 |
| Atomizing air (Bar) | 1.5 |
| Gun distance (inches) | 6 at 45° |
| Air temperature (°C.) | |
| Inlet | 60–75 |
| Exhaust | 36–40 |
| Bed temperature (°C.) | 32–35 |
| Pan rotation (rpm) | 10 |
| Tablet bed warming (min. jogging) | 10 |
| Total coating time (min.) | 65–80 |
| Post drying | |
| Inlet air temperature (°C.) | 60 |
| Drying time (min.) | 20 |
| Tablet weight gain (wt/wt %) | 2.7–3.0 |

EXAMPLE 2

The procedure of Example 1 is repeated but substituting glycerin plasticizer in lieu of the PEG 400.

EXAMPLE A

Prior Art—U.S. Pat. No. 4,543,370

A dry film-forming, water-dispersible powder was prepared as set forth in Example 1 supra in which the film-forming polymer is hydroxypropylmethylcellulose of the patent. The ingredients and the amounts were:

2000 g of hydroxypropylmethylcellulose (HPMC)
1000 g of titanium dioxide pigment
200 g of PEG 400
6.6 g of dioctyl sodium sulfosuccinate An aqueous dispersion of the powder was prepared and applied to ASA cores as in Example 1.

STABILITY TESTS

The coated tablets from Example 1 (WSCA) and Example A (HPMC) were subjected to physical testing such as friability, hardness and disintegration times so as to monitor for changes at accelerated temperature storage.

Coated tablets from Example 1 (WSCA) and Example A (HPMC) were placed in high density polyethylene (HDPE) bottles (100 count). The containers were closed with selfsealing lined metal caps and placed on stability station at RT, 35° C., 45° C. and 40° C./80% RH (open container).

Coated tablets from Example 1 (WSCA) exhibit no significant changes compared to initial after 2 week and 1 month accelerated temperature stability testing at 40° C./80% R and 45° C. (Table 1). Coated tablets from Example A (HPMC) exhibit moderate to severe physical instability relative to initial after 2 week and 1 month storage at 40° C./80% RH and 45° C. Coated tablet samples stored at 35° C. show no signs of instability.

Coated tablets from Example A (HPMC) exhibit moderate tablet sticking after 2 weeks storage at 40° C./80% RH. After 1 month storage at 45° C. and 40° C./80% RH, coated tablets from Example A (HPMC) exhibit severe sticking and tablet disintegration times increased rather significantly relative to initial. In addition, the coated tablets from Example A (HPMC) discolor at 45° C. and 40° C./80% RH. Coated tablets from Example 1 (WSCA) exhibit no changes relative to initial and are superior when compared to coated tablets from Example A (HPMC).

The data of Table 1 clearly demonstrates the unexpectedly superior coating properties of WSCA as against HPMC.

TABLE 1

Dry Blend Polymer Coating Stability Study
ASA Tablet Cores Coated in Accela Cota With WSCA (Example 1) and HPMC (Example A)

|  | Initial | 2 Weeks 40° C./80% RH | 1 Month 40° C./80% RH | 45° C. | 35° C. |
|---|---|---|---|---|---|
| Example 1 (WSCA) | | | | | |
| Weight, mg | 412.0 | 414.2 | 411.0 | 413.0 | 412.0 |
| Friability, % | 0.00 | 0.00 | 0.00 | 0.00 | 0.00 |
| Hardness, kg | 11.4 | 9.90 | 9.80 | 9.30 | 11.4 |
| Disintegration time, sec. | 36–48 | 30–50 | 30–46 | 30–46 | 30–48 |
| Appearance | Uniform, white Typical matt | No sticking No odor | No sticking No odor | No sticking No odor | No sticking No odor |
| Example A (HPMC) | | | | | |
| Weight, mg | 412.0 | 414.6 | 412.0 | 411.6 | 415.4 |
| Friability, % | 0.00 | 0.00 | 0.00 | 0.00 | 0.00 |
| Hardness, kg | 9.90 | 7.60 | 6.70 | 7.00 | 9.30 |
| Disintegration time, sec. | 53–89 | 35–134 | 30–120 | 45–160 | 56–80 |
| Appearance | Uniform, white Typical matt | Moderate sticking No odor | Severe sticking Slight odor, discolored | Severe sticking Discolored | No sticking No odor |

We claim:

1. A water-dispersible, particulate film-forming composition for use in film coating solid pharmaceutical dosages comprising a dry mixture produced by dry blending on a 100% weight basis in an amount of from about 50% to about 90%
   particles of water-soluble cellulose acetate
   pigment particles in an amount from about 0% to about 20%
   a plasticizing amount of plasticizer in an amount from about 2% to about 40% for the water-soluble cellulose acetate, and
   a surfactant in an amount from about 0.2% to about 2.0% which can be a separate component or a plasticizer having surfactant properties.

2. The composition of claim 1 wherein the surfactant is a separate component.

3. The composition of claim 1 wherein the plasticizer and surfactant is replaced with a liquid plasticizer having surfactant properties.

4. The composition of claim 1 wherein the plasticizer is selected from the group consisting of a polyethylene glycol (PEG) having a molecular weight of about 200 to about 8000, glycerin, propylene glycol, glyceryl triacetate, acetylated monoglyceride, triethyl citrate, tributyl citrate and acetyltriethyl citrate.

5. The composition of claim 3 wherein the plasticizer is a polyethylene glycol having a molecular weight of 400.

6. The composition of claim 1 a wherein the surfactant is dioctyl sodium sulfosuccinate.

7. The composition of claim 1 wherein the pigment particles are selected from the group consisting of FD&C and DC lakes, titanium dioxide, magnesium carbonate, talc, pyrogenic silica, iron oxides, channel black, riboflavin, carmine 40, curcumin, annatto and insoluble dyes.

8. The composition of claim 6 wherein the pigment particles are titanium dioxide.

9. A solid pharmaceutical or food dosage form comprising a matrix containing a pharmaceutically active or nutrient material, and a coating thereover, the coating comprising on a 100% weight basis a dry blended mixture of particles of water-soluble cellulose acetate in an amount of from about 50% to about 90%; pigment particles in an amount from about 0% to about 20%; a plasticizer for the water-soluble cellulose acetate in an amount from about 2% to 40%.

10. The composition of claim 8 produced by dry blending about 80% to about 90% of the water-soluble cellulose acetate; about 5% to about 10% of the plasticizer; about 5% to about 7.5% of the pigment and about 0.2% to about 2.0% of the surfactant.

11. The composition of claim 1 wherein the plasticizer is a polyethylene glycol having a molecular weight of 400.

12. The composition of claim 1 wherein the pigment is titanium dioxide.

13. The composition of claim 1 wherein the surfactant is dioctyl sodium sulfosuccinate.

14. A water-dispersible, particulate film-forming composition for use in film coating solid pharmaceutical dosages comprising a dry mixture produced by dry blending from about 50% to about 90% of water-soluble cellulose acetate particles; from about 2% to about 40% of a polyethylene glycol having a molecular weight of 400 as plasticizer for the water-soluble cellulose; from about 0% to about 20% of titanium dioxide pigment particles, and from about 0.2% to about 2.0% of dioctyl sodium sulfosuccinate surfactant.

15. A liquid film-forming coating composition for film coating solid pharmaceutical dosages comprising an aqueous dispersion of the composition of claim 1.

* * * * *